United States Patent [19]

Maki et al.

[11] Patent Number: 5,496,590
[45] Date of Patent: Mar. 5, 1996

[54] COMPOSITION FOR TREATING COPPER AND COPPER ALLOY SURFACES AND METHOD FOR THE SURFACE TREATMENT

[75] Inventors: Yoshiro Maki; Toshiko Nakagawa; Yoshiaki Furukawa; Minoru Outani; Takashi Haruta; Maki Yamanami; Sachiko Nakamura, all of Amagasaki, Japan

[73] Assignee: MEC Co., Ltd., Amagasaki, Japan

[21] Appl. No.: 289,271

[22] Filed: Aug. 11, 1994

[30] Foreign Application Priority Data

Aug. 11, 1993 [JP] Japan ................................. 5-217948
Sep. 7, 1993 [JP] Japan ................................. 5-246194

[51] Int. Cl.⁶ ............................. B05D 3/02; B05D 5/12
[52] U.S. Cl. ..................... 427/388.1; 427/96; 427/388.4
[58] Field of Search ................................. 427/388.1, 96, 427/388.4

[56] References Cited

U.S. PATENT DOCUMENTS

| | | | |
|---|---|---|---|
| 3,645,772 | 2/1972 | Jones | 427/162 |
| 4,098,720 | 7/1978 | Hwa | 106/14.14 |
| 4,612,049 | 9/1986 | Berner et al. | 106/14.13 |
| 4,812,363 | 3/1989 | Bell et al. | 427/410 |
| 5,064,723 | 11/1991 | Lawson | 156/330 |
| 5,089,304 | 2/1992 | Kuder | 427/388.1 |
| 5,211,881 | 5/1993 | Muller et al. | 427/388.4 |
| 5,275,694 | 1/1994 | Yamaguchi et al. | 156/656 |

FOREIGN PATENT DOCUMENTS 0428260  5/1991  European Pat. Off. .
0513831  11/1992  European Pat. Off. .
0551112  7/1993  European Pat. Off. .

OTHER PUBLICATIONS

Chemical Abstract No. 120:206406 of JP 04080374, Yoshioka et al, Mar. 1992.
Chemical Abstract No. 115:118782 of EP 428383, Kinoshita et al, May 1991.
Chemical Abstract No.: 120:250949 of JP 06002158, Kikukawa et al, Jun. 1992.
Database WPI, Derwent Publication Ltd., AN 93-232820, JP-A-5 156 475, Jun. 22, 1993.
Database WPI, Derwent Publications Ltd., AN 93-270088, JP-A-5 186 888, Jul. 27, 1993.

*Primary Examiner*—Diana Dudash
*Attorney, Agent, or Firm*—Oblon, Spivak, McClelland, Maier & Neustadt

[57] ABSTRACT

A composition for treating surfaces of copper and copper alloys comprising a specific imidazole derivative and water, and an acid or a water-soluble solvent. The composition can produce a heat resistant organic film with superior solderability when applied to surfaces of copper or copper alloys. It is particularly useful as a rust preventing agent for printed-wiring boards.

3 Claims, No Drawings

COMPOSITION FOR TREATING COPPER AND COPPER ALLOY SURFACES AND METHOD FOR THE SURFACE TREATMENT

BACKGROUND OF THE INVENTION

1. Field of the Invention

The present invention relates to a composition for treating surfaces of copper and copper alloys comprising a specific imidazole derivative, and to a method for treating surfaces of copper and copper alloys using this composition. The composition of the present invention is particularly useful as a rust preventing agent for printed-wiring boards.

2. Description of the Background Art

There are two methods for preventing rust in a circuit formed from copper or a copper alloy on a printed-wiring board and for maintaining good solderability. One is a method of covering the circuit with another metal and the other is a method of coating the circuit with organic films. Either of the two methods is used depending on the allowable cost, requirements for surface smoothness, and the like.

Examples of materials which form the organic film used in the last-mentioned method include a rosin-type coating material, which coats the entire printed-wiring board, and an alkylimidazole-type coating material which forms a film by a chemical reaction selectively on the copper circuit section.

The rosin-type coating material is used in a method for forming a film by coating, spraying, or soaking the entire printed-wiring board with a solution of a natural rosin, a rosin ester, a rosin-modified maleic acid resin, or the like, in an organic solvent, and then drying. However, this method involves a problem of impairing the working environment and the safety because of volatilization of the organic solvent. The treating plant must be provided with special equipment such as draft for air discharge.

Therefore, there have been desires for the use of water-soluble alkylimidazole-type coating materials which are excellent materials from the aspect of keeping a good working environment and safety. Films made from alkylimidazole-type coating materials, however, deteriorate when subjected to a high temperature, hindering the action of a postflux which is used during soldering and thus giving a rise to the drawback of poor solderability.

In recent years, a surface mounting method has become the most commonly used method for joining electronic parts on printed-wiring boards. This increases opportunities wherein printed-wiring boards are exposed to high temperatures, e.g., temporary mounting of the parts, reflow of solder pastes, and the like. For this reason, a water-soluble type surface treatment agent which has high heat resistance and exhibits excellent solderability, even when the printed-wiring boards have been exposed to high temperatures, is required.

In order to satisfy this requirement, Japanese Patent Laid-open (ko-kai) No. 124395/1991 discloses a coating agent comprising a benzimidazole derivative with a hydrogen atom, an alkyl group, or a phenyl group in 2-position of the imidazole ring.

In spite of the attempt of this laid-open patent to improve the heat resistance of alkyl imidazole type coating agents, the problems have not been resolved to the satisfaction of the industry.

Therefore, there have been a strong demands for a composition for treating surfaces of copper and copper alloys which exhibits improved heat resistance and provides a good working environment and safety, as well as for a method of the surface treatment.

In view of this situation, the present inventors have undertaken extensive studies in order to develop a water-soluble surface treating agent which does not require the use of volatile solvents and exhibits excellent solderability even after exposed a high temperature, and found that specific types of benzimidazole derivatives, represented by formulas (1) to (6) below or salts thereof, can produce a film which is heat resistant and exhibits excellent solderability. This finding has led to completion of the present invention.

SUMMARY OF THE INVENTION

Accordingly, an object of the present invention is to provide a composition for treating surfaces of copper and copper alloys comprising at least one imidazole compound of the following formulas (1) to (6),

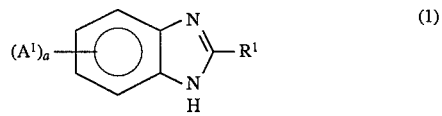

wherein $A^1$ is alkyl, alkenyl, alkynyl, aryl, aralkyl, phenylcarbonyl, or halogen, $R^1$ is an alkyl, alkenyl, alkynyl, or aryl group containing a halogen atom, and a is an integer of 0 to 4;

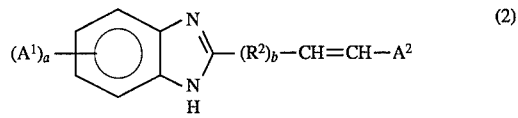

wherein $R^2$ is an alkylene, alkenylene, alkynylene, or arylene, $A^2$ is hydrogen, alkyl, alkynyl, aryl, aralkyl, phenylcarbonyl, or halogen, b is 0 or 1, and $A^1$ and a are the same as defined above;

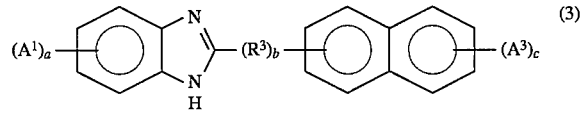

wherein $A^3$ is alkyl, alkenyl, alkynyl, aryl, aralkyl, phenylcarbonyl, or halogen, $R^3$ is alkylene, alkenylene, alkynylene, or arylene, c is an integer of 0 to 7, and $A^1$, a, and b are the same as defined above;

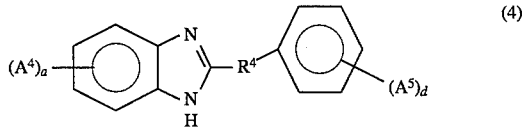

wherein $A^4$ is alkenyl, alkynyl, aryl, or aralkyl, $A^5$ is alkyl, alkenyl, alkynyl, aryl, aralkyl, phenylcarbonyl, or halogen, $R^4$ is alkylene, alkenylene, alkynylene, or arylene, d is an integer of 0 to 5, and a is the same as defined above;

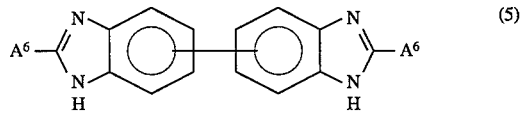

wherein $A^6$s are individually alkyl, alkenyl, alkynyl, aryl, aralkyl, or phenyl carbonyl;

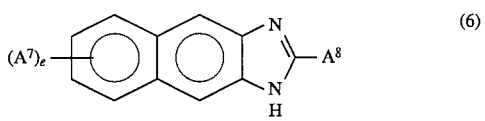

(6)

wherein $A^7$ is hydrogen, lower alkyl, or halogen, $A^8$ is alkyl, alkenyl, alkynyl, aryl, aralkyl, phenylcarbonyl, or halogen, and e is an integer of 0 to 6; or a salt thereof.

In a preferred embodiment of the present invention, the above composition further comprises an acid.

Another object of the present invention is to provide a method for treating surfaces of copper and copper alloys, which comprises applying an aqueous solution or an aqueous dispersion comprising at least one imidazole compound of the above-described formulas (1) to (6), or a salt thereof.

In a preferred embodiment of the above method, the above aqueous solution or aqueous dispersion further comprises an acid.

These and other objects, features, and advantages of the present invention will become more apparent from the following description of the preferred embodiments.

DETAILED DESCRIPTION OF THE INVENTION AND PREFERRED EMBODIMENTS

Examples of various groups in formulas (1) to (6) are as follows.

Compounds of formula (1)

$A^1$ in formula (1) is alkyl, alkenyl, alkynyl, aryl, aralkyl, or phenylcarbonyl group, or halogen.

Preferred alkyl groups are $C_{1-10}$ alkyl groups, such as methyl, ethyl, propyl, iso-propyl, butyl, tert-butyl, pentyl, tert-pentyl, hexyl, iso-hexyl, heptyl, 2-methyl-3-methylpentyl, octyl, 4-ethylhexyl, 5,5-dimethylheptyl, and decyl; preferred alkenyl groups are $C_{2-6}$ alkenyl groups, such as vinyl, allyl, 1,3-butadienyl, 2-methyl-2-butenyl, and 3-hexenyl; preferred alkynyl groups are $C_{2-6}$ alkynyl groups, such as ethynyl, 2-propynyl, 1-methyl-2-propynyl, 2-penten-4-ynyl, and 2-ethyl-3-butynyl; preferred aryl groups are $C_{6-10}$ aryl groups, such as phenyl, p-tolyl, styryl, 3-propylphenyl, and α-naphtyl; preferred aralkyl groups are $C_{7-12}$ aralkyl groups, such as benzyl, phenetyl, (3,5-xylyl)methyl, 4-phenylbutyl, 6-phenylhexyl, and 4-(4-vinylphenyl)butyl.

Preferred halogens in all imidazole compounds of formulas (1)–(6) are fluorine, chlorine, bromine, and iodine.

$R^1$ in formula (1) is alkyl, alkenyl, alkynyl, or aryl groups containing halogens. Examples of these groups include $C_{1-11}$ alkyl groups, $C_{2-9}$ alkenyl groups, $C_{2-9}$ alkynyl groups, and $C_{6-14}$ aryl groups containing one or more halogen atoms such as fluorine, chlorine, bromine, and iodine. Given as specific examples of $C_{1-11}$ alkyl groups containing halogen atoms are chloromethyl, 1-iodoethyl, 2-chloro-3-bromopropyl, 4-fluorobutyl, 3-(iodomethyl)butyl, 2,6-dichlorohexyl, 5-fluoroheptyl, 4,8-dichloro-6-bromooctyl, 3-methyl-3-ethyl-5-iodohexyl, 10-chlorodecyl, and 6-chloroundecyl; $C_{2-9}$ alkenyl groups containing halogen atoms, 2-bromovinyl, 2-chloro-1-propenyl, 1-fluoro-2-butenyl, 5-chloro-1-pentenyl, 6-bromo-1,3-hexadienyl, 5-chloro-2-heptenyl, 2-butyl-4-bromo-2-butenyl, 7,9-dibromo-1-nonenyl; $C_{2-9}$ alkynyl groups containing halogen atoms, 2-chloroethynyl, 1-chloro-2-propynyl, 1-(fluoromethyl)propynyl, 1-chloro-2-pentynyl, 1-(3-iodopropyl)-2-propynyl, 5-bromo-6-heptynyl, 1,3-difluoro-5-octynyl, 3-fluoro-1-nonynyl; and $C_{6-14}$ aryl groups containing halogen atoms, 4-chlorophenyl, 4-(chloromethyl)phenyl, 2-chloro-2-phenylvinyl, 5-iodo-α-naphthyl, 5-fluoro-9-anthryl.

Compounds of formula (2)

The same groups of $A^1$ in formula (1) mentioned above are given as examples of $A^1$ in formula (2).

$R^2$ in formula (2) is alkylene, alkenylene, alkynylene, or arylene. Preferred alkylene, alkenylene, alkynylene, or arylene groups are $C_{1-8}$ alkylene groups, such as are methylene, ethylene, propylene, butylene, 2-ethylpropylene, hexamethylene, 3,3-dimethylpentamethylene, and octamethylene groups; $C_{2-8}$ alkenylene groups, such as vinylene, propenylene, 2-butenylene, 2-pentenylene, 4-methylpentenylene, 4-ethylpentenylene, and 4-octenylene groups; $C_{2-8}$ alkynylene groups, such as ethynylene, propynylene, 2-butynylene, 4-pentynylene, 3-hexynylene, 1,2-dimethyl-4-pentynylene, and 2-methyl-6-heptynylene groups; and $C_{6-8}$ arylene groups, such as phenylene, 2-methyl-1,4-phenylene, and 2-ethyl-1,4-phenylene groups.

$A^2$ is in formula (2) is hydrogen, alkyl, alkynyl, aryl, aralkyl, phenylcarbonyl, or halogen. Preferred alkyl, alkynyl, aryl, and aralkyl groups are $C_{1-10}$ alkyl, $C_{2-7}$ alkynyl, $C_{6-11}$ aryl, and $C_{7-11}$ aralkyl groups. Specific examples of $C_{1-10}$ alkyl groups are methyl, ethyl, propyl, isopropyl, butyl, tert-butyl, pentyl, tert-pentyl, hexyl, isohexyl, heptyl, 2-methyl-3-metylpentyl, octyl, 4-ethylhexyl, 5,5-dimetylheptyl, and decyl groups; $C_{2-7}$ alkynyl groups, ethynyl, 2-propynyl, 1-methyl-2-propynyl, 2-penten-4-ynyl, 2-ethyl-3-butynyl, and 2,2-dimethylpentenyl; $C_{6-11}$ aryl groups, phenyl, p-tolyl, styryl, 3-propylphenyl, α-naphtyl, 4-methyl-α -naphthyl; and $C_{7-11}$ aralkyl groups, benzyl, phenethyl, (3,5,-xylyl)methyl, 4-phenylbutyl, and 6-phenylpentyl.

Compounds of formula (3)

The same examples as mentioned above are given for groups $A^1$ in formula (3).

$A^3$ is alkyl, alkenyl, alkynyl, aryl, aralkyl, phenylcarbonyl, or halogen. Preferred examples of alkyl, alkenyl, alkynyl, aryl, and aralkyl groups are $C_{1-6}$ alkyl groups, such as methyl, ethyl, propyl, isopropyl, butyl, tert-butyl, tert-pentyl, and hexyl groups; $C_{2-4}$ alkenyl groups, such as vinyl, allyl, and 1,3-butadienyl groups; $C_{2-4}$ alkynyl groups, such as ethynyl, 2-propynyl, 1-methyl-2-propynyl groups; $C_{6-8}$ aryl groups, such as phenyl, p-tolyl, styryl groups; and $C_{7-8}$ aralkyl groups, such as benzyl group and phenethyl group.

$R^3$ in formula is alkylene, alkenylene, alkynylene, or arylene. Preferred examples of alkylene, alkenylene, alkynylene, or arylene groups include are $C_{1-5}$ alkylene groups, such as are methylene, ethylene, propylene, butylene, and 2-methylbutylen and groups; $C_{2-5}$ alkenylene groups, such as vinylene, propenylene, 2-butenylene, and 3-vinylpropylene groups; $C_{2-5}$ alkynylene groups, such as ethynylene, propynylene, 2-butynylene, and 2-pentynylene groups; and $C_{6-8}$ arylene groups, such as phenylene, 2-methyl-1,4-phenylene, and 2-ethyl-1,4-phenylene groups.

Compounds of formula (4)

$A^4$ in formula (4) is alkenyl, alkynyl, aryl, or aralkyl group. Given as preferred examples of $C_{2-6}$ alkenyl groups, such as vinyl, allyl, 1,3-butadienyl, 2-methyl-2-butenyl, and 3-hexenyl groups; $C_{2-6}$ alkynyl groups, such as ethynyl, 2-propynyl, 1-methyl-2-propynyl, 2-penten-4-ynyl, and 2-ethyl-3-butynyl groups; $C_{6-10}$ aryl groups, such as phenyl, p-tolyl, styryl, 3-propylphenyl, and α-naphthyl groups; $C_{7-12}$ aralkyl groups, such as benzyl, phenethyl, (3,5,-xylyl)methyl, 4-phenylbutyl, 6-phenylhexyl, and 4-(4-vinylphenyl)butyl groups.

$R^4$ in formula (4) is alkylene, alkenylene, alkynylene, or arylene. Preferred examples of alkylene, alkenylene, alkynylene, and arylene groups include $C_{1-6}$ alkylene groups, such as methylene, ethylene, propylene, butylene, 2-ethylpropylene, and hexamethylene groups; $C_{2-4}$ alkenylene groups, such as vinylene, propenylene, and 2-butenylene groups; $C_{2-4}$ alkynylene groups, such as ethynylene, propynylene, and 2-butynylene groups; and $C_{6-8}$ arylene groups, such as phenylene, 2-methyl-1,4-phenylene, and 2-ethyl-1,4-phenylene groups.

$A^5$ in formula (4) is alkyl, alkenyl, alkynyl, aryl, aralkyl, phenylcarbonyl, or halogen.

Preferred alkyl, alkenyl, alkynyl, aryl, and aralkyl, groups are $C_{1-10}$ alkyl groups, such as methyl, ethyl, propyl, isopropyl, butyl, tert-butyl, pentyl, tert-pentyl, hexyl, iso-hexyl, heptyl, 2-methyl-3-methylpentyl, octyl, 4-ethylhexyl, 5,5-dimethylheptyl, and decyl; $C_{2-7}$ alkenyl groups, such as vinyl, allyl, 1,3-butadienyl, 2-methyl-2-butenyl, 3-hexenyl, and 1-heptenyl; $C_{2-7}$ alkynyl groups, such as ethynyl, 2-propynyl, 1-methyl-2-propynyl, 2-penten-4-ynyl, 2-ethyl-3-butynyl, and 2,2-dimethylpentynyl; $C_{6-11}$ aryl groups, such as phenyl, p-tolyl, styryl, 3-propylphenyl, α-naphtyl, and 4-methyl-α-naphthyl; and aralkyl groups are $C_{7-11}$ aralkyl groups, such as benzyl, phenetyl, (3,5-xylyl)methyl, 4-phenylbutyl, and 6-phenylpentyl.

Compounds of formula (5)

In formula (5), two $A^6$s are individually alkyl, alkenyl, alkynyl, aryl, aralkyl, or phenyl carbonyl.

Examples of alkyl groups include $C_{1-9}$ alkyl groups, such as methyl, ethyl, propyl, isopropyl, butyl, tert-butyl, pentyl, tert-pentyl, hexyl, isohexyl, heptyl, 2-methyl-3-metylpentyl, octyl, and 4-ethylheptyl groups; examples of alkenyl groups are $C_{2-7}$ alkenyl groups, such as vinyl, allyl, 1,3-butadienyl, 2-methyl-2-butenyl, 3-hexenyl, and 1-heptenyl groups; examples of alkynyl groups are $C_{2-7}$ alkynyl groups, such as ethynyl, 2-propynyl, 1-methyl-2-propynyl, 2-penten-4-ynyl, 2-ethyl-3-butynyl, and 2,2-dimethylpentynyl groups; examples of aryl groups are $C_{6-10}$ aryl groups, such as phenyl, p-tolyl, styryl, 3-propylphenyl, and α-naphthyl groups; and examples of aralkyl groups are $C_{7-10}$ aralkyl groups, such as benzyl, phenethyl, (3,5,-xylyl)methyl, and 4-phenylbutyl groups.

Compounds of formula (6)

$A^7$ in formula (6) is hydrogen, lower alkyl, or halogen. Preferred lower alkyl groups are $C_{1-3}$ alkyl groups such as methyl, ethyl, propyl, and isopropyl groups.

$A^8$ in formula (6) is alkyl, alkenyl, alkynyl, aryl, aralkyl, phenylcarbonyl, or halogen.

Given as preferred alkyl, alkenyl, alkynyl, and aryl, aralkyl groups are $C_{1-11}$ alkyl groups, such as methyl, ethyl, propyl, isopropyl, butyl, tert-butyl, pentyl, tert-pentyl, hexyl, isohexyl, heptyl, 2-methyl-3-metylpentyl, octyl, 4-ethylhexyl, 5,5-dimetylheptyl, and undecyl groups; $C_{2-9}$ alkenyl groups, such as vinyl, allyl, 1,3-butadienyl, 2-methyl-2-butenyl, 3-hexenyl, 1-heptenyl, 2-butyl-2-butenyl, 1-nonenyl; $C_{2-9}$ alkynyl groups, such as ethynyl, 2-propynyl, 1-methyl-2-propynyl, 2-penten-4-ynyl, 2-ethyl-3-butynyl, 2,2-dimethylpentenyl, 5-octynyl, and 1-nonynyl groups; $C_{6-13}$ aryl groups, such as phenyl, p-tolyl, styryl, 3-propylphenyl, α-naphthyl, 5-ethyl-α-naphthyl, and 4-(p-tolyl)phenyl groups; and $C_{7-13}$ aralkyl groups, such as benzyl, phenethyl, (3,5, -xylyl)methyl, 4-phenylbutyl, 6-phenylpentyl, 6-phenylhexyl, 4-(4-vinylphenyl)butyl, and 3-(α-naphthyl)propyl groups.

The imidazole compounds of formulas (1)–(6) can be prepared, for example, by reacting an o-phenylenediamine compound and a carboxylic acid in the presence of p-toluene sulfonic acid under heating.

The compounds of the following Tables 1–7 can be given as specific examples of the compounds of formulas (1) to (6), which can be preferably used as the active ingredient of the composition of surface treatment agent for copper and copper alloys of the present invention.

TABLE 1

| Formula (1) | $A^1$ | a | $R^1$ |
|---|---|---|---|
| 6-chloro-2-(4-chlorophenylmethyl)benzimidazole | Cl | 1 | 4-chlorophenylmethyl |
| 2-(2-(4-chlorophenyl)ethyl)benzimidazole | | 0 | 2-(4-chlorophenyl)ethyl |
| 2-chloromethylbenzimidazole | | 0 | chloromethyl |
| 5-ethyl-2-chloromethylbenzimidazole | ethyl | 1 | chloromethyl |
| 5-nonyl-2-(2-chloro-3-bromopropyl)benzimidazole | nonyl | 1 | 2-chloro-3-bromopropyl |
| 5-vinyl-2-(7-chloroheptyl)benzimidazole | vinyl | 1 | 7-chloroheptyl |
| 6-styryl-2-(2-bromovinyl)benzimidazole | styryl | 1 | 2-bromovinyl |
| 5-(1-propenyl)-2-(2-chloro-2-phenylvinyl)benzimidazole | 1-propenyl | 1 | 2-chloro-2-phenylvinyl |
| 6-butadienyl-2-(2-chloroethynyl)benzimidazole | butadienyl | 1 | 2-chloroethynyl |
| 4-ethynyl-2-(1-bromo-2-propynyl)benzimidazole | ethynyl | 1 | 1-bromo-2-propynyl |
| 6-propynyl-2-(4-chlorophenyl)benzimidazole | propynyl | 1 | 4-chlorophenyl |
| 5-phenyl-2-(5-iodo-α-naphtyl)benzimidazole | phenyl | 1 | 5-iodo-α-naphtyl |
| 6-α-naphtyl-2-(5-fluoro-9-anthryl)benzimidazole | α-naphtyl | 1 | 5-fluoro-9-anthryl |
| 7-p-toryl-2-(3-methyl-4-bromophenyl)benzimidazole | p-toryl | 1 | 3-methyl-4-bromophenyl |
| 4-phenyl-5-propyl-2-(4-chloromethylphenyl)benzimidazole | phenyl | 1 | 4-chloromethylphenyl |
| | propyl | 1 | |

TABLE 2

| Formula (2) | $A^1$ | a | $R^2$ | b | $A^2$ |
|---|---|---|---|---|---|
| 2-(3-phenyl-2-propenyl)benzimidazole | | 0 | methylene | 1 | phenyl |
| 6-chloro-2-(3-phenyl-2-propenyl)benzimidazole | Cl | 1 | methylene | 1 | phenyl |
| 4-methyl-2-propenylbenzimidazole | methyl | 1 | methylene | 1 | H |
| 5-nonyl-2-styrylbenzimidazole | nonyl | 1 | phenylene | 1 | H |
| 6-vinyl-2-propenylbenzimidazole | vinyl | 1 | methylene | 1 | H |
| 7-ethynyl-2-butadienylbenzimidazole | ethynyl | 1 | vinylene | 1 | H |

TABLE 2-continued

| Formula (2) | $A^1$ | a | $R^2$ | b | $A^2$ |
|---|---|---|---|---|---|
| 4-phenyl-2-vinylbenzimidazole | phenyl | 1 | — | 0 | H |
| 4-methyl-5-ethyl-2-styrylbenzimidazole | methyl<br>ethyl | 1<br>1 | phenylene | 1 | H |
| 4-p-tolyl-5-ethyl-2-propenylbenzimidazole | p-tolyl<br>ethyl | 1<br>1 | methylene | 1 | H |
| 4-methyl-5-ethyl-6-phenyl-2-(2-tolylvinyl)benzimidazole | methyl<br>ethyl<br>phenyl | 1<br>1<br>1 | — | 0 | tolyl |
| 6-(3,5-xylyl)-2-(1-chloro-2-butenyl)benzimidazole | 3,5-xylyl | 1 | methylene | 1 | chloromethyl |

TABLE 3

| Formula (3) | $A^1$ | a | $R^3$ | b | $A^3$ | c |
|---|---|---|---|---|---|---|
| 2-(α-naphthylethyl)benzimidazole | — | 0 | ethylene | 1 | — | 0 |
| 5-chloro-2-(α-naphthylmethyl)benzimidazole | Cl | 1 | methylene | 1 | — | 0 |
| 5-methyl-2-(α-naphthylmethyl)benzimidazole | methyl | 1 | methylene | 1 | — | 0 |
| 2-(α-naphthylmethyl)benzimidazole | — | 0 | methylene | 1 | — | 0 |
| 2-(β-naphthylmethyl)benzimidazole | — | 0 | methylene | 1 | — | 0 |
| 2-(β-naphthyl)benzimidazole | — | 0 | — | 0 | — | 0 |
| 2-(α-naphthyl)benzimidazole | — | 0 | — | 0 | — | 0 |
| 4-vinyl-2-(2-(β-naphthyl)ethyl)benzimidazole | vinyl | 1 | ethylene | 1 | — | 0 |
| 6-isobutyl-2-(2-(β-naphthyl)ethyl)benzimidazole | i-butyl | 1 | ethylene | 1 | — | 0 |
| 7-octyl-2-(3-(4-methyl-α-naphthyl)propyl)benzimidazole | octyl | 1 | propylene | 1 | methyl | 1 |
| 4-chloro-2-(4-(3-hexyl-β-naphthyl)butyl)benzimidazole | Cl | 1 | butylene | 1 | hexyl | 1 |
| 5-benzyl-2-(2-(5-chloro-α-naphthyl)isopropyl)benzimidazole | benzyl | 1 | i-propylene | 1 | Cl | 1 |

TABLE 4

| Formula (3) | $A^1$ | a | $R^3$ | b | $A^3$ | c |
|---|---|---|---|---|---|---|
| 2-(5-chloro-α-naphthyl)benzimidazole | — | 0 | — | 0 | Cl | 1 |
| 4-chloro-6-ethyl-2-(2-(α-naphthyl)ethyl)benzimidazole | Cl<br>ethyl | 1<br>1 | ethylene | 1 | — | 0 |
| 6-cyclohexyl-2-(2-(5-bromo-6-ethylnaphthyl)ethyl)-benzimidazole | cyclohexyl | 1 | ethylene | 1 | Br<br>ethyl | 1<br>1 |
| 4-phenyl-2-(3-vinyl-2-(α-naphthyl)propyl)benzimidazole | phenyl | 1 | 3-vinylpropylene | 1 | — | 0 |
| 6-decyl-2-(8-(β-naphthyl)octyl)benzimidazole | decyl | 1 | octylene | 1 | — | 0 |
| 2-(2-(7-phenetyl-β-naphthyl)ethyl)benzimidazole | — | 0 | ethylene | 1 | phenetyl | 1 |
| 2-(6-pyridyl-3-methyl-β-naphthylmethyl)benzimidazole | — | 0 | methylene | 1 | pyridyl<br>methyl | 1<br>1 |
| 2-(3-(7-benzoyl-β-naphthyl)propyl)benzimidazole | — | 0 | propylene | 1 | benzoyl | 1 |
| 2-(7-indenyl-β-naphthylmethyl)benzimidazole | — | 0 | methylene | 1 | indenyl | 1 |
| 2-(7-chloroethyl-β-naphthylmethyl)benzimidazole | — | 0 | methylene | 1 | chloroethyl | 1 |
| 4,5-dimethyl-2-(7-(4-ethynylphenyl)-α-naphthyl)benzimidazol | methyl | 2 | — | 0 | 4-ethynylphenyl | 1 |

TABLE 5

| Formula (4) | $A^4$ | a | $R^4$ | $A^5$ | d |
|---|---|---|---|---|---|
| 5-vinyl-2-(4-(4-propylphenyl)phenyl)benzimidazole | vinyl | 1 | phenylene | propyl | 1 |
| 4-ethynyl-2-(6-(3-chloro-4-cinnamylphenyl)hexyl)benzimidazole | ethynyl | 1 | hexylene | 3-chloro<br>4-cinnamyl | 1<br>1 |
| 2-(4-(3,4-dimethylphenyl)phenylethyl)benzimidazole | — | 0 | ethylene | 3,4-dimethylphenyl | 1 |
| 4-benzyl-2-(2-(3,5-xylyl)ethyl)benzimidazole | benzyl | 1 | ethylene | methyl | 2 |

TABLE 6

| Formula (5) | $A^6$ | $A^6$ |
|---|---|---|
| 2,2'-diheptyl-5,5'-dibenzimidazole | heptyl | heptyl |
| 2-methyl-2'-ethyl-5,5'-dibenzimidazole | methyl | ethyl |
| 2-nonyl-2'-isopropyl-5,5'-dibenzimidazole | nonyl | iso-propyl |
| 2-vinyl-2'-styryl-4,5'-dibenzimidazole | vinyl | styryl |
| 2-ethynyl-2'-phenyl-4,4'-dibenzimidazole | ethynyl | phenyl |
| 2-naphthyl-2'-p-tolyl-5,5'-dibenzimidazole | naphthyl | p-tolyl |
| 2-(5-phenetylpentyl)-2'-cinnamyl-5,5'-dibenzimidazole | 5-phenetylpentyl | cinnamyl |
| 2-phenetyl-2'-phenylcarbonyl-4,5'-dibenzimidazole | phenetyl | phenylcarbonyl |
| 2-(2-(4-chlorophenyl)ethyl)-2'-(3-phenylbutyl)-5,5'-dibenzimidazole | 2-(2-(4-chlorophenyl)ethyl) | phenylbutyl |

TABLE 7

| Formula (6) | $A^7$ | e | $A^8$ |
|---|---|---|---|
| 2-methylnaphthoimidazole | — | 0 | methyl |
| 5-chloro-2-nonylnaphthoimidazole | chloro | 1 | nonyl |
| 4,5-dichloro-2-vinyl-naphthoimidazole | chloro | 2 | vinyl |
| 5-methyl-2-ethynyl-naphthoimidazole | methyl | 1 | ethynyl |
| 4,5-dimethyl-2-phenyl-naphthoimidazole | methyl | 2 | phenyl |
| 2-phenylcarbonylnaphthoimidazole | — | 0 | phenylcarbonyl |
| 5-ethyl-2-styrylnaphthoimidazole | ethyl | 1 | styryl |
| 5,6,8-trimethyl-2-benzyl-naphthoimidazole | methyl | 3 | benzyl |

There are no specific limitations as to the salts for the above-described benzimidazole compounds of formulas (1)–(6). Included are salts of an organic acid such as formic acid, acetic acid, propionic acid, glycolic acid, n-butyric acid, isobutyric acid, acrylic acid, crotonic acid, isocrotonic acid, valeric acid, 3-methylbutyric acid, 2-methylbutyric acid, caproic acid, enanthic acid, caprylic acid, trans-2-methyl-2-pentenoic acid, phenylacetic acid, 5-phenylvaleric acid, 4-phenylvaleric acid, benzoic acid, ω-cyclohexylbutyric acid, α-naphthaleneacetic acid, diphenylacetic acid, oxalic acid, malonic acid, succinic acid, adipic acid, maleic acid, acetylene dicarboxylic acid, pimelic acid, suberic acid, 2-n-butylmalonic acid, phthalic acid, monochloroacetic acid, trichloroacetic acid, monobromoacetic acid, tribromoacetic acid, 3-chloropropionic acid, 2-chloropropionic acid, 2-chlorobutyric acid, 2-chlorovaleric acid, 2-chlorocaproic acid, 2-chloroenanthic acid, 2-chlorocaprilic acid, 2-bromopropionic acid, 3-bromopropionic acid, 2-bromobutyric acid, 4-bromobutyric acid, 2-bromovaleric acid, 5-bromovaleric acid, 2-bromocaproic acid, 6-bromocaproic acid, 2-bromoenanthic acid, 7-bromoenanthic acid, p-chlorophenylacetic acid, p-bromophenylacetic acid, lactic acid, oxybutyric acid, glyceric acid, tartaric acid, malic acid, citric acid, or the like; an inorganic acid such as hydrochloric acid, sulfuric acid, nitric acid, phosphoric acid, or the like.

Although the amount of imidazole compound in the composition for surface treatment of the present invention is varied depending on the solubility of the imidazole compound in the solvent and the like, an amount in the range of of 0.1–5.0% by weight is normally preferable.

The imidazole compounds of formulas (1) to (6) are normally insoluble in water. Some of the salts of these compounds are also insoluble in water. These are therefore made into an aqueous solution or an aqueous dispersion by using one or more of said acids, in an amount of 0.1–20% by weight, or a water-soluble solvent, in an amount of 50% by weight or less, or combination of the acid and the solvent.

Given as examples of water-soluble solvents are methanol, ethanol, iso-propanol, ethylene glycol monomethyl ether, ethylene glycol monoethyl ether, and the like.

A metal compound may be added to the composition of the present invention for improving its film-forming ability or heat resistance of the films. Included in examples of such metal compounds are zinc acetate, zinc hydroxide, zinc sulfide, zinc phosphate, zinc oxide, zinc chloride, lead acetate, lead hydroxide, iron chloride, iron oxide, copper chloride, copper oxide, copper hydroxide, copper bromide, copper phosphate, copper carbonate, copper acetate, copper sulfate, copper oxalate, copper formate, nickel acetate, nickel sulfide, and the like. Other additives of various types which have been conventionally used for surface treating agents may be also added as required. Further, the film-forming capability can be increased by adjusting the acid concentration.

There are no specific limitations to the method of preparation of the composition of the present invention. It may be prepared, for example, by mixing an imidazole compound with an aqueous solution of an acid or by mixing a salt of an imidazole compound and an acid with an aqueous solution of other kind of acid.

The composition of the present invention thus prepared can produce a heat resistant organic film with superior solderability by applying it on surfaces of copper or copper alloys.

Japanese Patent Application No. 217948/1993 filed on Aug. 11, 1993 and No. 246194/1993 filed on Sep. 7, 1993 are herein incorporated as references.

Other features of the invention will become apparent in the course of the following description of the exemplary embodiments which are given for illustration of the invention and are not intended to be limiting thereof.

EXAMPLES

Example 1

<Preparation of 6-chloro-2-(4-chlorophenylmethyl)benzimidazole (Compound of formula (1)) and the surface treating composition using this compound>

142.5 g (1 mol) of 4-chloro-o-phenylenediamine, 170.5 g (1 mol) of 4-chlorophenylacetic acid, and 190 g (1 mol) of p-toluene sulfonic acid monohydrate (hereinafter called PTS) were thoroughly blended and heated using a mantle heater while stirring. The temperature was raised to 200° C. in 30 minutes, then the mixture was heated at 200° to 220° C. for 3 hours until almost all steam was evaporated. The reaction mixture thus obtained was poured into aqueous ammonia and stirred to solidify. The solid was washed with water and dried to produce a purple powder. This powder was recrystallized with a solvent to obtain 0.5 g of white, needle-shaped crystals of 6-chloro-2-(4-chlorophenylmethyl)benzimidazole. The compound was dissolved in as much an amount of acetic acid as can dissolve this compound. The solution thus obtained was added to 100 ml of water containing 0.04 g of cupric chloride to obtain the composition of the present invention.

A 1 cm×5 cm×0.3 mm test specimen was prepared from a copper plate by the surface cleaning process comprising defatting, washing with water, dipping in a microetching solution (MEC Bright CB-801, trademark, a product of MEC Co.) at 30° C. for 1 minutes, and washing with water. This test specimen was immersed in the the above solution of 6-chloro-2-(4-chlorophenylmethyl)benzimidazole for one minute at 40° C., washed with water and dried, then heated in a hot air circulation apparatus for 10 minutes at 200° C. A soldering flux (AP-4626, trademark, a product of MEC Co.) was applied to this test specimen and the soldering wettability test by the Meniscograph method was carried out. The results are shown in Table 1, wherein $t_1$ indicates the time from start of the immersion until a peak of buoyancy from surface tension is reached, which is determined from the rate of immersion and the time at which wetting commences, and $t_2$ is the time from start of immersion until buoyancy from surface tension becomes zero, i.e. the time when the contact angle reaches 90°. The smaller these values, the greater the soldering wettability.

Example 2

<Preparation of 2-(2-(4-chlorophenyl)ethyl)benzimidazole (Compound of formula (1)) and the surface treating composition using this compound>

2-(2-(4-chlorophenyl)ethyl)benzimidazole was prepared in the same manner as in Example 1 from o-phenylenediamine, 3-(4-chlorophenyl)propionic acid, and PTS. The composition of the present invention was prepared using this compound and its solder wettability was tested in the same manner as in Example 1. The results are shown Table 8.

Example 3

<Preparation of 2-(3-phenyl-2-propenyl)benzimidazole (Compound of formula (2)) and the surface treating composition using this compound>

2-(3-phenyl-2-propenyl)benzimidazole was prepared in the same manner as in Example 1 from o-phenylenediamine, 4-phenyl-3-butylenic acid, and PTS. The composition of the present invention was prepared using this compound and its solder wettability was tested in the same manner as in Example 1. The results are shown Table 8.

Example 4

<Preparation of 6-chloro-2-(3-phenyl-2-propenyl)benzimidazole (Compound of formula (2)) and the surface treating composition using this compound>

The title compound was prepared in the same manner as in Example 1 from 4-chloro-o-phenylenediamine, 4-phenyl-3-butylenic acid, and PTS. The composition of the present invention was prepared using this compound and its solder wettability was tested in the same manner as in Example 1. The results are shown Table 8.

Example 5

<Preparation of 2-(α-naphthylmethyl)benzimidazole (Compound of formula (3)) and the surface treating composition using this compound>

The title compound was prepared in the same manner as in Example 1 from o-phenylenediamine, α-naphthalene acetic acid, and PTS. The composition of the present invention was prepared using this compound and its solder wettability was tested in the same manner as in Example 1. The results are shown Table 8.

Example 6

<Preparation of 2-(α-naphthylethyl)benzimidazole (Compound of formula (3)) and the surface treating composition using this compound>

The title compound was prepared in the same manner as in Example 1 from o-phenylenediamine, 3-naphthalene propionic acid, and PTS. The composition of the present invention was prepared using this compound and its solder wettability was tested in the same manner as in Example 1. The results are shown Table 8.

Example 7

<Preparation of 5-chloro-2-(α-naphthylmethyl)benzimidazole (Compound of formula (3)) and the surface treating composition using this compound>

The title compound was prepared in the same manner as in Example 1 from 4-chloro-o-phenylenediamine, α-naphthalene acetic acid, and PTS. The composition of the present invention was prepared using this compound and its solder wettability was tested in the same manner as in Example 1. The results are shown Table 8.

Example 8

<Preparation of 5-methyl-2-(α-naphthylmethyl)benzimidazole (Compound of formula (3)) and the surface treating composition using this compound>

The title compound was prepared in the same manner as in Example 1 from 4-methyl-o-phenylenediamine, α-naphthalene acetic acid, and PTS. The composition of the present invention was prepared using this compound and its solder wettability was tested in the same manner as in Example 1. The results are shown Table 8.

Example 9

<Preparation of 2,2'-diheptyl-5,5'-dibenzimidazole (Compound of formula (5)) and the surface treating composition using this compound>

The title compound was prepared in the same manner as in Example 1 from 3,3'-diaminobenzidine, octanic acid (2 mols), and PTS. The composition of the present invention was prepared using this compound and its solder wettability was tested in the same manner as in Example 1. The results are shown Table 8.

Comparative Example 1

A comparative composition was prepared in the same manner as in Example 1, except that 2-nonylbenzimidazole was used instead of 6-chloro-2-(4-chlorophenylmethyl)benzimidazole. The solder wettability was tested on this composition in the same manner as in Example 1, The results are shown Table 8.

TABLE 8

| | Soldering wettability (sec) | |
|---|---|---|
| | $t_1$ | $t_2$ |
| Example 1 | 0.40 | 1.12 |
| Example 2 | 0.48 | 1.33 |

TABLE 8-continued

|  | Soldering wettability (sec) | |
| --- | --- | --- |
|  | $t_1$ | $t_2$ |
| Example 3 | 0.51 | 1.38 |
| Example 4 | 0.45 | 1.25 |
| Example 5 | 0.41 | 1.20 |
| Example 6 | 0.45 | 1.28 |
| Example 7 | 0.41 | 1.13 |
| Example 8 | 0.46 | 1.26 |
| Example 9 | 0.50 | 1.72 |
| Comparative Example 1 | 0.78 | 3.20 |

Obviously, numerous modifications and variations of the present invention are possible in light of the above teachings. It is therefore to be understood that within the scope of the appended claims, the invention may be practiced otherwise than as specifically described herein.

We claim:

1. A method for treating surfaces of copper and copper alloys, which comprises applying an aqueous solution or an aqueous dispersion comprising at least one imidazole derivative of the following formulas (1) to (6), or a salt thereof,

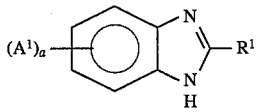
(1)

wherein $A^1$ is alkyl, alkenyl, alkynyl, aryl, aralkyl, phenylcarbonyl, or halogen, $R^1$ is an alkyl, alkenyl, alkynyl, or aryl group containing a halogen atom, and a is an integer of 0 to 4;

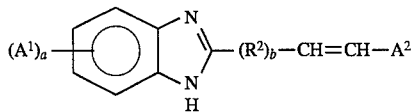
(2)

wherein $R^2$ is an alkylene, alkenylene, alkynylene, or arylene, $A^2$ is hydrogen, alkyl, alkynyl, aryl, aralkyl, phenylcarbonyl, or halogen, b is 0 or 1, and $A^1$ and a are the same as defined above;

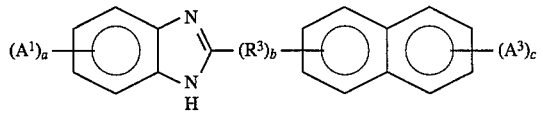
(3)

wherein $A^3$ is alkyl, alkenyl, alkynyl, aryl, aralkyl, phenylcarbonyl, or halogen, $R^3$ is alkylene, alkenylene, alkynylene, or arylene, c is an integer of 0 to 7, and $A^1$, a, and b are the same as defined above;

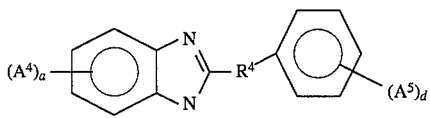
(4)

wherein $A^4$ is alkenyl, alkynyl, aryl, or aralkyl, $A^5$ is alkyl, alkenyl, alkynyl, aryl, aralkyl, phenylcarbonyl, or halogen, $R^4$ is alkylene, alkenylene, alkynylene, or arylene, d is an integer of 0 to 5, and a is an integer of 1 to 4;

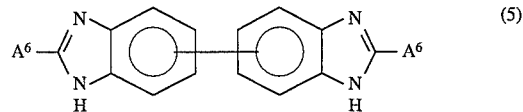
(5)

wherein $A^6$s are individually alkyl, alkenyl, alkynyl, aryl, aralkyl, or phenyl carbonyl;

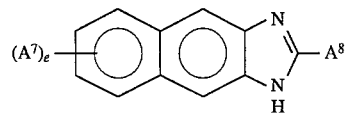
(6)

wherein $A^7$ is hydrogen, lower alkyl, or halogen, $A^8$ is alkyl, alkenyl, alkynyl, aryl, aralkyl, phenylcarbonyl, or halogen, and e is an integer of 0 to 6.

2. The method according to claim 1, wherein said aqueous solution or aqueous dispersion further comprises an acid selected from the group consisting of formic acid, acetic acid, propionic acid, glycolic acid, n-butyric acid, isobutyric acid, acrylic acid, crotonic acid, isocrotonic acid, valeric acid, 3-methylbutyric acid, 2-methylbutyric acid, caproic acid, enanthic acid, caprilic acid, trans-2-methyl-2-pentenoic acid, phenylacetic acid, 5-phenylvaleric acid, 4-phenylvaleric acid, benzoic acid, ω-cyclohexylbutyric acid, α-naphthaleneacetic acid, diphenylacetic acid, oxalic acid, malenic acid, succinic acid, adipic acid, maleic acid, acetylene dicarboxylic acid, pimelic acid, suberic acid, 2-n-butylmalonic acid, phthalic acid, monochloroacetic acid, trichloroacetic acid, monobromoacetic acid, tribromoacetic acid, 3-chloropropionic acid, 2-chloropropionic acid, 2-chlorobutyric acid, 2-chlorovaleric acid, 2-chlorocaproic acid, 2-chloroenanthic acid, 2-chlorocaprilic acid, 2-bromopropionic acid, 3-bromopropionic acid, 2-bromobutyric acid, 4-bromobutyric acid, 2-bromovaleric acid, 5-bromovaleric acid, 2-bromocaproic acid, 6-bromocaproic acid, 2-bromoenanthic acid, 7-bromoenanthic acid, p-chlorophenylacetic acid, p-bromophenylacetic acid, lactic acid, oxybutyric acid, glyceric acid, tartaric acid, malic acid, citric acid, hydrochloric acid, sulfuric acid, nitric acid and phosphoric acid.

3. The method according to claim 1, wherein said aqueous solution or aqueous dispersion further comprising water-soluble solvent selected from the group consisting of methanol, ethanol, iso-propanol, ethylene glycol monomethyl ether, and ethylene glycol monoethyl ether.

* * * * *

UNITED STATES PATENT AND TRADEMARK OFFICE
CERTIFICATE OF CORRECTION

PATENT NO. : 5,496,590
DATED : March 5, 1996
INVENTOR(S) : Yoshiro MAKI ET AL

It is certified that error appears in the above-identified patent and that said Letters Patent is hereby corrected as shown below:

Column 1, line 65, "been a strong demands" should read --been strong demands--.

Column 2, line 8, "exposed a high temperature" should read --exposed to a high temperature--.

Column 7, Table 4, Formula (3), line 4, "6-cyclohexyl-2-(2-(5-bromo-6-ethylnaphthyl)ethyl)-benzimidazole" should read --6-cyclohexyl-2-(2-(5-bromo-6-ethylnaphthyl)ethyl)benzimidazole--.

Column 9, line 56, "an amount in the range of" should read --an amount in the range--.

Column 11, line 9, " in the the above" should read --in the above--.

Column 12, line 57, "as in Example 1," should read --as in Example 1.--.

UNITED STATES PATENT AND TRADEMARK OFFICE
CERTIFICATE OF CORRECTION

PATENT NO. : 5,496,590
DATED : March 5, 1996
INVENTOR(S) : Yoshiro MAKI et al.

It is certified that error appears in the above-identified patent and that said Letters Patent is hereby corrected as shown below:

Column 14, line 36, "malenic" should read --malonic--.

Signed and Sealed this

Fourteenth Day of July, 1998

*Attest:*

*Attesting Officer*

BRUCE LEHMAN
*Commissioner of Patents and Trademarks*